United States Patent [19]

Miller

[11] Patent Number: 5,447,503
[45] Date of Patent: Sep. 5, 1995

[54] GUIDING CATHETER TIP HAVING A TAPERED TIP WITH AN EXPANDABLE LUMEN

[75] Inventor: Jay F. Miller, Miami, Fla.

[73] Assignee: Cordis Corporation, Miami Lakes, Fla.

[21] Appl. No.: 234,709

[22] Filed: Apr. 28, 1994

Related U.S. Application Data

[63] Continuation of Ser. No. 34,595, Mar. 22, 1993, abandoned, which is a continuation of Ser. No. 744,885, Aug. 14, 1991, abandoned.

[51] Int. Cl.⁶ .......................................... A61M 29/02
[52] U.S. Cl. ............................................... 604/280
[58] Field of Search .......................... 604/280–283, 604/93–96, 104–109, 160; 606/198, 191

[56] References Cited

U.S. PATENT DOCUMENTS

| | | | |
|---|---|---|---|
| 3,228,846 | 1/1966 | Bryan | 176/18 |
| 4,581,025 | 11/1983 | Timmermans | 604/264 |
| 4,850,975 | 7/1989 | Furukawa | 604/170 |
| 4,893,623 | 1/1990 | Rosenbluth | 606/192 |
| 4,899,729 | 2/1990 | Gill et al. | 606/198 |
| 4,912,733 | 3/1990 | Gluntz | 376/371 |
| 4,920,954 | 8/1988 | Alliger et al. | 124/24 |
| 4,921,479 | 5/1990 | Grayzel | 604/53 |
| 5,211,654 | 5/1993 | Kaltenbach | 606/191 |

FOREIGN PATENT DOCUMENTS

1082992  6/1960  Germany.

*Primary Examiner*—C. Fred Rosenbaum
*Assistant Examiner*—Manuel Mendez
*Attorney, Agent, or Firm*—Thomas R. Vigil

[57] ABSTRACT

An angioplasty system including a guiding catheter for inserting into and traversing a human blood vessel. The guiding catheter receives and guides a balloon catheter and/or a PTCA guidewire into an area to be treated in a blood vessel. The catheter has an elongate body with a proximal end and a distal end and is made out of a flexible and dimensionally stable material to afford an expandable lumen and spring properties at the distal end. The distal end has a longitudinal slot for enabling one side wall portion of the catheter wall to slide under the other side wall portion for achieving partially overlapping catheter wall portions and for creating a spiral fold tip. The spiral fold tip is tapered to facilitate movement of the tip through a blood vessel.

9 Claims, 2 Drawing Sheets

FIG. 1
FIG. 2
FIG. 3
FIG. 4
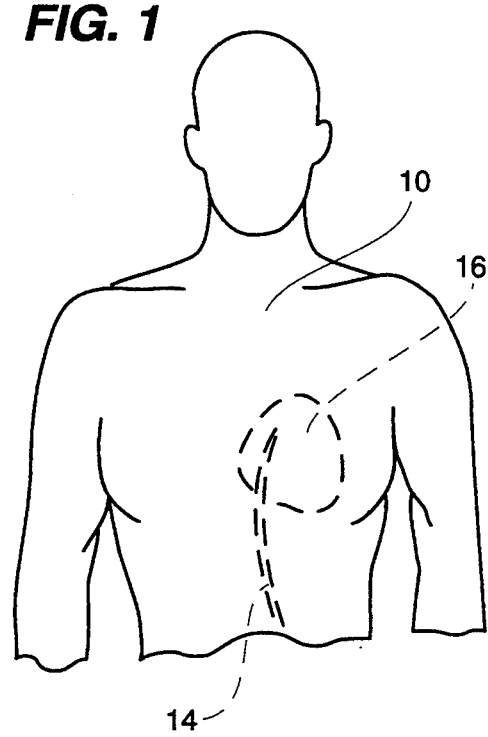
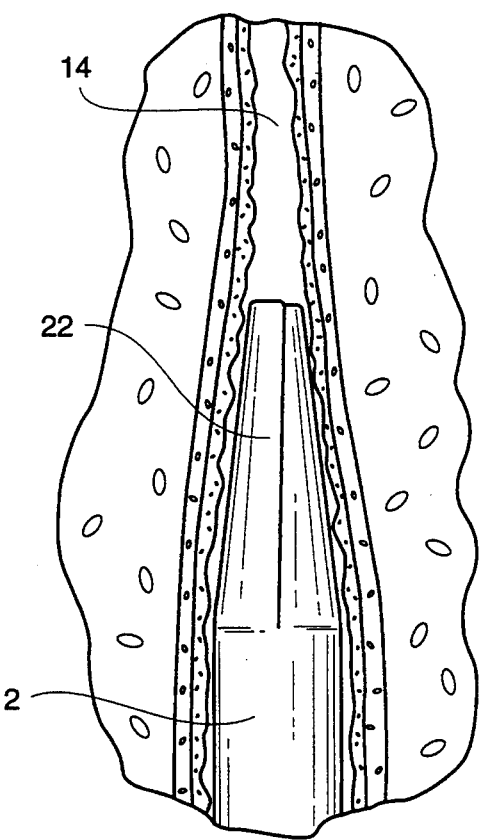
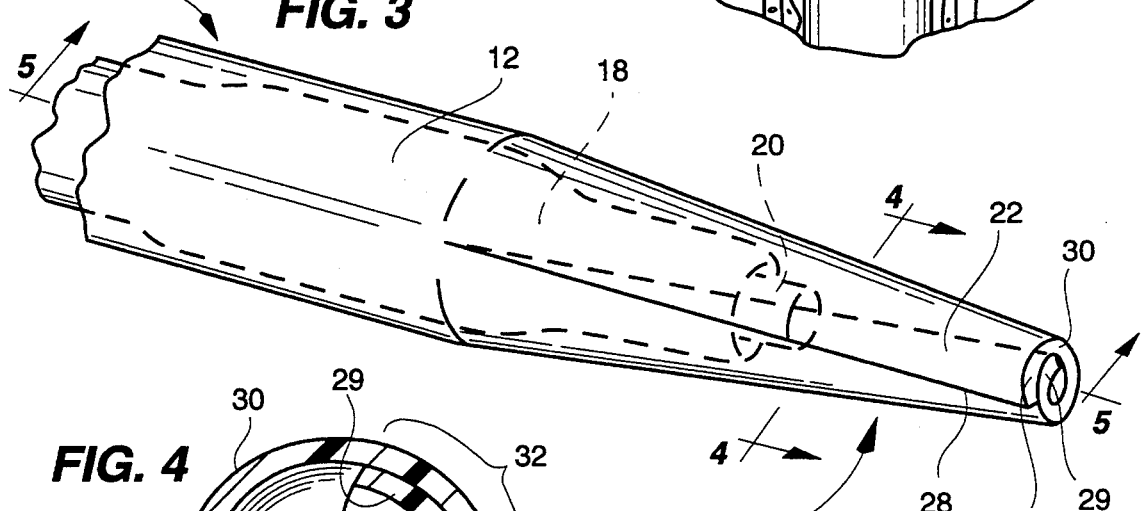
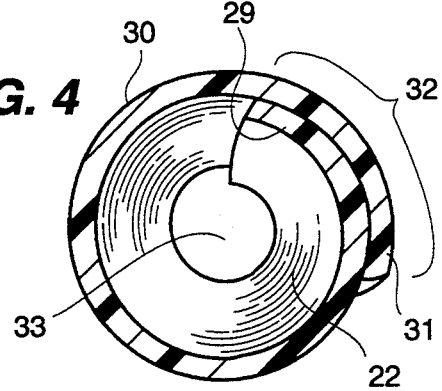

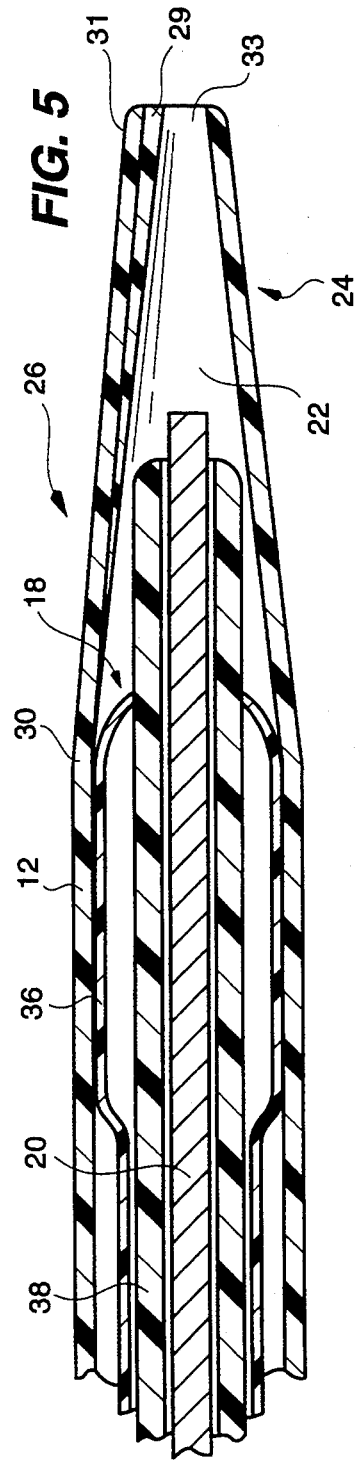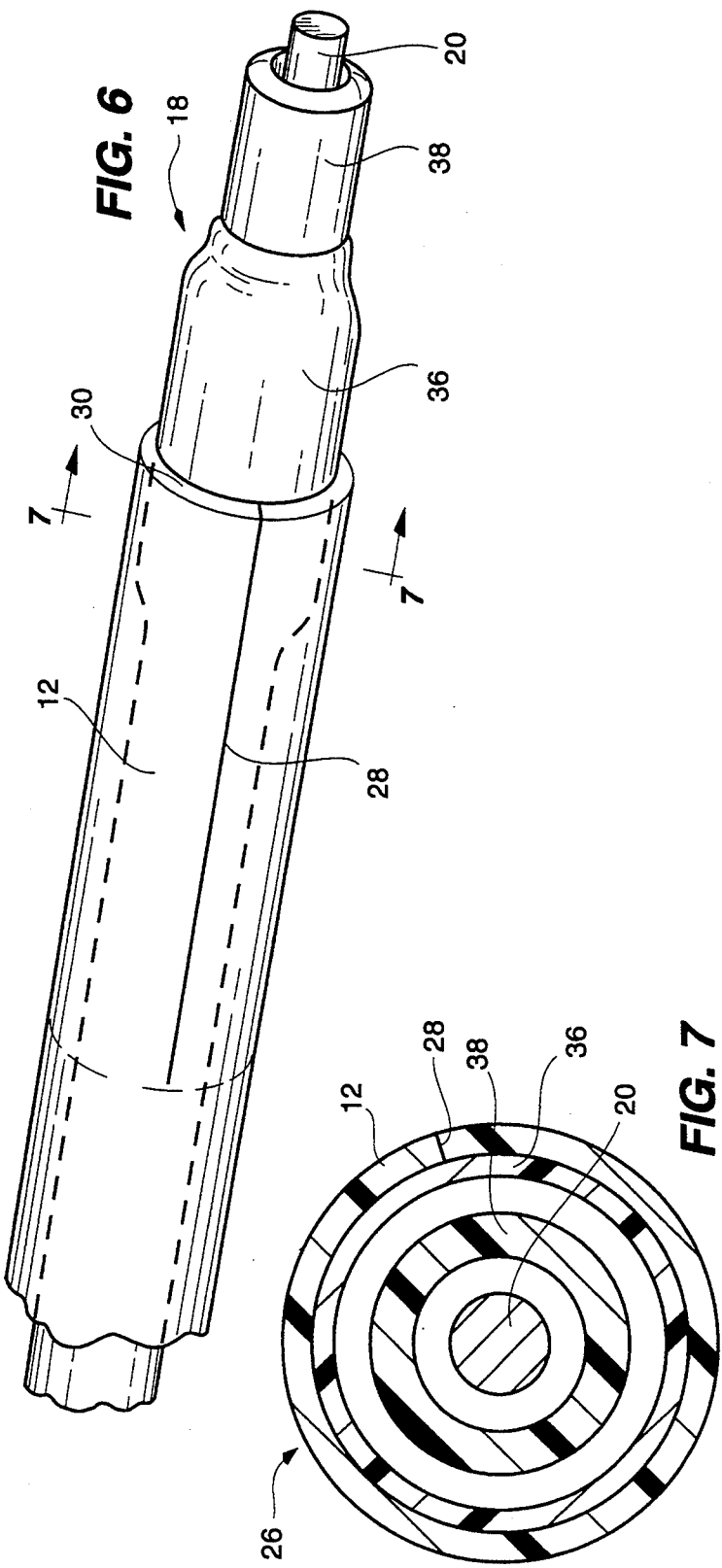

1

GUIDING CATHETER TIP HAVING A TAPERED TIP WITH AN EXPANDABLE LUMEN

This is a continuation of application Ser. No. 08/034,595 filed Mar. 22, 1993 now abandoned, which is a continuation of U.S. Ser. No. 07/744,885 filed Aug. 14, 1991 and now abandoned.

BACKGROUND OF THE INVENTION

1. Field of the Invention

The present invention relates to an angioplasty system used in angiographic examinations and treatments. More specifically, the present invention relates to a catheter for guiding and receiving a PTCA guidewire or a balloon catheter while being inserted and moved in a femoral artery or carotid artery. To enable the catheter to move within the blood vessel without hurting the patient, the distal end of the catheter includes a tapered tip with an expandable lumen, the taper facilitating movement of the catheter in a vessel and the expandability of the lumen facilitating ejection of the balloon catheter from the guiding catheter once an operating position is reached.

2. Description of the Related Art Including Information Disclosed Under 37 CFR §§1.97–1.99

As will be described in greater detail hereinafter, the catheter of the present invention differs from prior catheters by having a tapered tip with an expandable lumen for traversing a vessel easily and for enclosing a balloon catheter on a PTCA guidewire until the catheter has reached an area in a vessel to be treated.

SUMMARY OF THE INVENTION

According to the present invention there is provided an angioplasty guiding catheter assembly which comprises a balloon mounted on a catheter forming a balloon catheter or mounted on a guidewire forming a balloon-on-a-wire guidewire. A vascular catheter which has a length sufficient to extend from outside a human body through an arterial system to the heart and which includes an elongate tubular body having a lumen, a proximal end, a distal end portion integral with the tubular body and a distal end. The tubular body is sized to receive the balloon mounted on a catheter or mounted on a guidewire. The vascular catheter is made out of a flexible, dimensionally stable, non-metal, synthetic material. The distal end portion only has a longitudinal slot for enabling one side wall portion of the catheter wall on one side of the slot to be slid under the other side wall portion in the distal end portion on the other side of the slot for achieving partially overlapping catheter wall portions and for creating a spiral folded tip with an expandable and collapsible lumen. The spiral folded tip of the distal end portion is tapered to facilitate movement of the tip through a blood vessel. The overlapping catheter wall portions have a spring force which, after a distortion of only the tip to a larger diameter lumen, urges the wall portions back to the spiral folded and tapered tip formation after the balloon is moved out of the vascular catheter and after the balloon is pulled back into the vascular catheter.

Further according to the invention there is provided a method for performing an angioplasty procedure using the angioplasty assembly described above, the method comprising the steps of: inserting a guidewire into a vascular system to an area where a blood vessel is constricted to a cross section less than its normal cross section; inserting the vascular catheter over the guidewire and into the vascular system; withdrawing the initially inserted guidewire from the vascular catheter; inserting the balloon folded to a small volume and mounted on a catheter or mounted on a guidewire into the vascular catheter and then out of the spiral, folded tip causing the lumen of the spiral, folded tip to be expanded as the balloon is moved out of the spiral, folded tip and into the blood vessel to the area of constriction, followed by collapsing of the spiral, folded tip substantially back to its original shape; inflating the balloon to expand the area of constriction; deflating the balloon; withdrawing the deflated unfolded balloon into the spiral, folded tip causing it to expand as the balloon is pulled therethrough, the spring force of the spiral, folded tip compressing the unfolded deflated balloon to at least a size which will fit easily into the lumen of the tubular body of the catheter; and, withdrawing the deflated balloon from the tubular body.

BRIEF DESCRIPTION OF THE DRAWINGS

FIG. 1 is a front elevational view of a patient undergoing catheterization for heart blood vessel angioplasty and shows a catheter inserted percutaneously into and through the femoral artery to the heart.

FIG. 2 is an enlarged longitudinal sectional view through a blood vessel and its surroundings as it is being traversed by a catheter tip constructed according to the teachings of the present invention.

FIG. 3 is an enlarged perspective view of a distal end of a catheter of an angioplasty system constructed according to the teachings of the present invention.

FIG. 4 is a transverse sectional view of a tapered and spiral fold tip of the catheter shown in FIG. 3 and is taken along line 4—4 of FIG. 3.

FIG. 5 is a longitudinal sectional view of the catheter shown in FIG. 3 and is taken along line 5—5 of FIG. 3.

FIG. 6 is a perspective view of the catheter shown in FIG. 3 with components therein telescoped forwardly.

FIG. 7 is a transversed sectional view of the catheter shown in FIG. 6 and is taken along line 7—7 of FIG. 6.

DESCRIPTION OF THE PREFERRED EMBODIMENT(S)

Referring now to FIG. 1, there is illustrated therein a patient 10 undergoing catheterization for heart angioplasty. For this purpose, a guiding catheter 12 of a catheter assembly 13 of an angioplasty system is inserted percutaneously into and traversed through the femoral artery 14 into the heart 16. Then a balloon catheter 18 with a guidewire 20 therein of the catheter assembly 13 is inserted through the guiding catheter 12 to place a distal end portion 21 of the balloon catheter 18 and PTCA guidewire 20 within the heart 16.

To reach the heart 16, or another area to be treated, the guiding catheter 12 is pushed through a blood vessel, such as the femoral artery 14, as can be seen in FIG. 2, until a desired position, i.e., area of treatment, is reached. A tapered tip 22 in a distal end portion 24 of the guiding catheter 12 allows smooth and cautious movement through the vessel.

An angioplasty system of a preferred embodiment, as shown in FIG. 3, includes the catheter assembly 13 comprising the guiding catheter 12, the balloon catheter 18 and the PTCA guidewire 20. A distal end portion 24 of the guiding catheter 12 has a longitudinal slit or slot 28 within the tip 22, to allow one side wall portion 29 of catheter wall 30 at the slot 28 to slide under the opposite side wall portion 31 for creating an overlap 32 of the wall portions 29 and 31 and for spiral folding of the walls of the tip 22. The degree of overlap increases progressively from the beginning of the longitudinal slot 28 outwardly and reaches its maximum at the open end 33 of the tip 22 of the guiding catheter 12.

The guiding catheter 12 is made out of a flexible and dimensionally stable plastic material. By forcing the tip 22 into its permanently overlapping position, the tip 22 is formed of a spiral fold. The shape memory of the plastic material gives the spiral fold tip 22 spring properties. The progressively increasing of the overlap causes at the same time a decrease in the diameter of lumen 34 in the tapered tip 22 of the guiding catheter 12 to establish the taper.

FIGS. 4 and 5 show the overlapping catheter wall portions 29 and 31 and the spiral fold in tapered tip 22 in sectional views. FIG. 5 also shows the balloon catheter 18 with its balloon portion 36 and its main body portion 38 and the PTCA guidewire 20 partly inside the balloon catheter 18 and guidewire 20.

FIGS. 6 and 7 show the balloon catheter 18 and guidewire 20 just after they are guided out of the tip 22. The balloon catheter 18 inside the guiding catheter 12 has an outer diameter greater than the smallest inner diameter of the tip 22 and forces open the overlapping catheter wall portions 29 and 31 to enlarge the lumen 34 of the tip 22, while passing through the tip 22. The flexible plastic material of the tip 22 of the guiding catheter 12 with its spring properties maintains a close relationship to the balloon catheter 18, while being enlarged and urges back to its initial tapered and spiral fold position once the balloon catheter 18 is withdrawn into the guiding catheter 12. This helps prevent coring and enhances tracking.

An advantage of the present invention is, that it permits a great reduction of the outer diameter of the tapered tip 22 of the guiding catheter 12 by a returning of the tip 22 into its initial tapered and spiral fold position, once the balloon catheter 18 is withdrawn into the guiding catheter 12.

The spiral fold tip 22 is made to hold its shape and profile by application of a force to the overlap area which inputs a "shape memory". This force can be: mechanical force; heat-by conduction or radiation; cohesive force; or adhesive force. The method of choice is driven by the material from which the tip 22 is made.

When a guidewire or fixed wire PTA/PTCA catheter is pushed into the tip 22, the axial compression forces of the tip are translated into hoop stresses. The translated stresses cause the spiral overlap fold to expand and admit the guidewire or other member to pass into the expandable lumen 34 with the tip 22 maintaining a tight fit around the member.

From the foregoing description, it will be apparent that the angioplasty system of the present invention has a number of advantages, some of which have been described above and others of which are inherent in the invention. Also, modifications can be made to the tapered and spiral fold tip 22 of the guiding catheter 12 of the present invention without departing from the teachings of the invention. Accordingly, the scope of the invention is only to be limited as necessitated by the accompanying claims.

I claim:

1. An angioplasty guiding catheter assembly comprising:
    a balloon;
    said balloon being mounted on a catheter forming a balloon catheter or mounted on a guidewire forming a balloon-on-a-wire guidewire;
    a vascular catheter having a length sufficient to extend from outside a human body into an arterial system for performing an angioplasty procedure and including an elongate tubular body a proximal end, a lumen, a distal end portion integral with said tubular body and a distal end, said tubular body being sized to receive said balloon mounted on a catheter or mounted on a guidewire at said proximal end and allowing said balloon mounted on a catheter or mounted on a guidewire to pass completely through said tubular body and extend beyond said distal end;
    said vascular catheter and said distal end portion each being made out of a flexible, dimensionally stable, non-metal, synthetic material;
    said distal end portion only having a longitudinal slot for enabling one side wall portion of the catheter wall on one side of said slot to be slid under the other side wall portion in said distal end portion on the other side of said slot for achieving partially overlapping catheter wall portions and for creating a spiral folded tip with an expandable and collapsible lumen;
    said spiral folded tip of said distal end portion being tapered to facilitate movement of said tip through a blood vessel; and
    said overlapping catheter wall portions having a spring force which, after a distortion of only said tip by said balloon when said uninflated balloon initially passes through said tip and by said balloon catheter or said guidewire when said balloon extends beyond said tip to a larger diameter lumen, urges said wall portions back to said spiral folded and vascular catheter when said balloon and said balloon catheter or said guidewire are retracted from said distal end portion of said tubular body.

2. The angioplasty assembly of claim 1 wherein said distal end is incorporated into said elongate tubular body.

3. The angioplasty of claim 1 wherein said distal end is attached to said elongate tubular body.

4. The angioplasty assembly of claim 1 wherein the portion of overlapping of said catheter wall portions increases with a decreasing of the diameter of said tapered and spiral fold tip.

5. The angioplasty assembly of claim 1 wherein said tapered and spiral fold tip has an expandable lumen and said material of said catheter has a shape memory for urging wall portions of the tip back into their initially tapered and spiral fold position and, when said wall portions are expanded and enlarged, for maintaining a close relationship to the enlarging member, for maintaining a close relationship to an enlarging member moved therethrough.

6. For use in an angioplasty guiding catheter assembly, a vascular catheter for receiving a balloon mounted on a catheter and forming a balloon catheter or mounted on a guidewire and forming a balloon-on-a-wire guidewire, said vascular catheter having a length sufficient to extend from outside a human body into an arterial system for performing an angioplasty procedure and including an elongate tubular body having a proximal end, a lumen, a distal end portion integral with said tubular body and a distal end, said tubular body being sized to receive the balloon mounted on a catheter or mounted on a guidewire at said proximal end and allowing the balloon mounted on a catheter or mounted on a guidewire to pass completely through said tubular body and extend beyond said distal end;

said vascular catheter and said distal end portion each being made out of a flexible, dimensionally stable, non-metal synthetic material;

said distal end portion only having a longitudinal slot for enabling one side wall portion of the catheter wall on one side of said slot to be slid under the other side wall portion in said distal end portion on the other side of said slot for achieving partially, overlapping catheter wall portions and for creating a spiral, folded tip with an expandable and collapsible lumen;

said spiral folded tip of said distal end portion being tapered to facilitate movement of said tip through a blood vessel; and said overlapping catheter wall portions having a spring force which, after distortion of only said tip by the balloon when the uninflated balloon initially passes through the tip and by the balloon catheter or the guidewire when the balloon extends beyond said tip to a larger diameter lumen, urges said wall portions back to said spiral folded and tapered tip formation when the balloon and the balloon catheter or the guidewire are retracted from the distal end portion of the tubular body.

7. A method for performing an angioplasty procedure using an angioplasty guiding catheter assembly comprising:

a balloon;

the balloon being folded to a small volume and mounted on a catheter forming a balloon catheter or mounted on a guidewire forming a balloon-on-a-wire guidewire;

a vascular catheter which has a length sufficient to extend from outside a human body into an arterial system for performing an angioplasty procedure and including an elongate tubular body having a proximal end, a distal end portion integral with the tubular body and a distal end, the tubular body being sized to receive the balloon mounted on a catheter or mounted on a guidewire at the proximal end and allowing the balloon mounted on a catheter or mounted on a guidewire to pass completely through the tubular body and extend beyond the distal end;

the vascular catheter and the distal end portion each being made out of a flexible, dimensionally stable, non-metal, synthetic material;

the distal end portion only having a longitudinal slot for enabling one side wall portion of the catheter wall on one side of the slot to be slid under the other side wall portion in the distal end portion on the other side of the slot for achieving partially overlapping catheter wall portions and for creating a spiral folded tip with an expandable and collapsible lumen;

the spiral, folded tip of the distal end portion being tapered to facilitate movement of the spiral, folded tip through a blood vessel; and the overlapping catheter wall portions having a spring force which, after a distortion of only the spiral, folded tip by the balloon when the uninflated balloon initially passes through the tip and the balloon catheter or the guidewire when the balloon extends beyond the distal end to a larger diameter lumen, urges the wall portions back to the spiral folded and tapered tip formation when the balloon catheter or the guidewire is retracted from the distal end portion of the tubular body, the method comprising the steps of:

inserting a guidewire into a vascular system to an area where a blood vessel is constricted to a cross section less than its normal cross section;

inserting the vascular catheter over the guidewire and into the vascular system;

withdrawing the initially inserted guidewire from the vascular catheter;

inserting the balloon folded to a small volume and mounted on a catheter or mounted on a guidewire into the vascular catheter and then out of the spiral, folded tip causing the lumen of the spiral, folded tip to be expanded as the balloon passes through the distal end portion and the spiral, folded tip and completely beyond the tip into the blood vessel to the area of constriction, followed by partial collapsing of the spiral, folded tip around the guidewire;

inflating the balloon to expand the area of constriction;

deflating the balloon;

withdrawing the deflated unfolded balloon into the spiral, folded tip causing it to expand as the balloon is pulled therethrough, the spring force of the spiral, folded tip compressing the unfolded deflated balloon to at least a size which will fit easily into the lumen of the tubular body of the vascular catheter; and, upon withdrawing the balloon completely from the tip collapsing the balloon to substantially its original shape.

8. An angioplasty guiding catheter comprising:

an elongate tubular body having a length sufficient to extend from outside a human body into an arterial system for performing an angioplasty procedure and including a proximal end, a lumen, a distal end portion integral with said tubular body and a distal end, said tubular body being sized to receive an elongate member, such as a balloon catheter or a balloon-on-a-wire guidewire at said proximal end and allowing the balloon mounted on a catheter or mounted on a guidewire to pass completely through said tubular body and extend beyond said distal end;

said catheter and said distal end portions each being made out of a flexible, dimensionally stable, non-metal synthetic material;

said distal end portion only having a longitudinal slot for enabling one side wall portion of the catheter wall on one side of said slot to be slid under the other side wall portion in said distal end portion on the other side of said slot for achieving partially overlapping catheter wall portions and for creating a spiral folded tip with an expandable and collapsible lumen;

said spiral folded tip of said distal end portion being tapered to facilitate movement of said tip through a blood vessel; and said overlapping catheter wall portions having a spring force which, after a distortion of only said by the balloon when the uninflated balloon initially passes through said tip and by the balloon catheter or the guidewire when the balloon extends beyond said tip to a larger diameter lumen, urges said wall portions back to said spiral fold and tapered tip formation when the balloon and the balloon catheter or the guidewire are retracted from said distal end portion of said tubular body.

9. A catheter for guiding and receiving elongate members, such as a guidewire or a balloon catheter, while traversing a human or animal blood vessel, said catheter comprising:

an elongate tubular body having a length sufficient to extend from outside a human body into an arterial system for performing an angioplasty procedure and including a proximal end, a lumen, a distal end portion integral with said tubular body and a distal end, said tubular body being sized to receive an elongate member, such as a guidewire, a balloon catheter or a balloon-on-a-wire guidewire at the proximal end and allowing said balloon mounted on a catheter or mounted on a guidewire to pass completely through said tubular body and extend beyond said distal end;

said catheter and said distal end portions each being made out of a flexible, dimensionally stable, non-metal synthetic material;

said distal end portion only having a longitudinal slot for enabling one side wall portion of the catheter wall on one side of said slot to be slid under the other side wall portion in said distal end portion on the other side of said slot for achieving partially overlapping catheter wall portions and for creating a spiral folded tip with an expandable and collapsible lumen;

said spiral folded tip of said distal end portion being tapered to facilitate movement of said tip through a blood vessel; and said overlapping catheter wall portions having a spring force which, after a distortion of only said tip by the balloon when the uninflated balloon initially passes through said tip and by the balloon catheter or the guidewire when the balloon extends beyond said tip to a larger diameter lumen, urges said wall portions back to said spiral fold and tapered tip formation when the balloon and the balloon catheter or the guidewire are retracted from said distal end portion of said tubular body.

* * * * *

UNITED STATES PATENT AND TRADEMARK OFFICE
CERTIFICATE OF CORRECTION

PATENT NO. : 5,447,503
DATED : September 5, 1995
INVENTOR(S) : Jay F. Miller

It is certified that error appears in the above-indentified patent and that said Letters Patent is hereby corrected as shown below:

Column 4, line 7, "body a" should be --body having a--.

Signed and Sealed this

Fifth Day of December, 1995

Attest:

BRUCE LEHMAN

*Attesting Officer*   *Commissioner of Patents and Trademarks*